(12) United States Patent
Baturin et al.

(10) Patent No.: US 8,855,395 B2
(45) Date of Patent: Oct. 7, 2014

(54) CONDITIONAL LIKELIHOOD MATERIAL DECOMPOSITION AND METHODS OF USING THE SAME

(71) Applicants: Pavlo Baturin, Rochester, NY (US); Mark E. Shafer, Fairport, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 96 days.

(21) Appl. No.: 13/732,767

(22) Filed: Jan. 2, 2013

(65) Prior Publication Data

US 2014/0185896 A1   Jul. 3, 2014

(51) Int. Cl.
*G06K 9/00* (2006.01)
*G06T 7/00* (2006.01)

(52) U.S. Cl.
CPC .................................. *G06T 7/0012* (2013.01)
USPC ........................................... 382/131; 378/62

(58) Field of Classification Search
USPC ........ 382/100, 128–132; 378/1, 4, 18, 21, 41, 378/51, 62, 70, 87
See application file for complete search history.

(56) References Cited

U.S. PATENT DOCUMENTS

| 7,346,204 B2 * | 3/2008 | Ito ................................. 382/132 |
| 7,693,256 B2 * | 4/2010 | Brahme et al. ................... 378/41 |
| 2012/0045108 A1 * | 2/2012 | Shechter ....................... 382/131 |

* cited by examiner

*Primary Examiner* — Shefali Goradia

(57) ABSTRACT

Embodiments of methods and apparatus are disclosed for obtaining a radiographic phase-contrast digital computed tomography imaging system and methods for same that can include obtaining a first and second plurality of 2D projection images over a range of scan angles, generating at least two statistically independent reconstructed images of an object from the first plurality of 2D projection images and the second plurality of 2D projection images, determining a material property as a function of volume for each of at least two materials represented in the projection images, using a conditional likelihood determination comprising the material property as a function of volume and the at least two statistically independent reconstructed images to differentiate the at least two materials in a reconstructed image of the object.

18 Claims, 19 Drawing Sheets

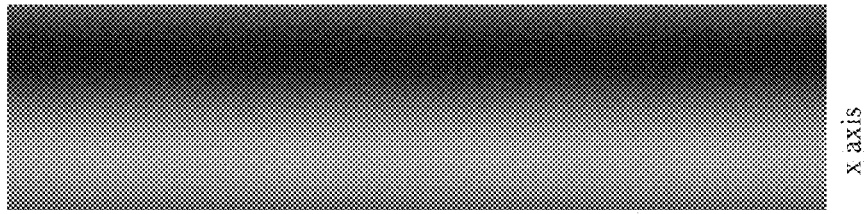
FIG. 19

CONDITIONAL LIKELIHOOD MATERIAL DECOMPOSITION AND METHODS OF USING THE SAME

FIELD OF THE INVENTION

The application generally relates to digital x-ray imaging methods/system, and more specifically, to methods and/or systems for material identification/decomposition based on statistical independence of plurality of images of an object using spectral computed tomography (CT) or phase contrast imaging (PCI) CT techniques.

BACKGROUND

One of the important tasks of diagnostic radiation imaging is the ability to differentiate between different materials. Such a task is traditionally applied to absorption images obtained by conventional medical x-ray images devices, which are based on the attenuation through photoelectric absorption of the x-rays penetrating the object to be imaged. However, in the clinically acceptable x-ray imaging energy range (e.g. 10-140 keV), soft tissues (e.g., vessels, cartilages, lungs, breast tissues) have absorption values of similar magnitude. That provides a poor contrast between such materials, which significantly complicates or makes almost unfeasible the material differentiation task.

The problem of low contrast in soft tissues can be addressed with phase contrast imaging (PCI) techniques. The principle of PCI is based on the wave nature of x-rays, where refraction and diffraction properties need to be considered. As an electromagnetic wave, the x-ray is usually characterized by its frequency, amplitude, and phase. When an electromagnetic wave penetrates a medium, its amplitude is attenuated and its phase is shifted. In x-ray technology, the refractive index n of a material can be expressed by a complex number $$n = 1 - \delta + i\beta. \quad (1)$$

The imaginary part $\beta$ contributes to the attenuation of the amplitude and the real part $\delta$ is responsible for the phase shift. It has been shown that $\beta$ is about $10^3$ to $10^4$ times larger than $\delta$. While conventional medical imaging records only information of $\beta$, the information of $\delta$ is completely lost.

In recent years, several PCI techniques have been explored to make use of the phase shift through the object. Phase shift, as an addition to absorption information, can be beneficial to material decomposition techniques. Related art material decomposition methods rely on the differences in absorption values of the materials. When the absorption values are so close that ambiguity in material differentiation is created, the phase shift information can be used instead. Additionally spectral techniques (e.g. dual energy techniques), where plurality of images (e.g. absorption and/or phase shift) is created, can be employed to aid the material differentiation. Although, the combination of image plurality and PCI technique can yield significantly better material identification, material misidentification is still possible when code values of different materials are close enough to create the ambiguity. In such a situation, there is a need for improved material decomposition techniques.

SUMMARY OF THE INVENTION

An aspect of this application is to advance the art of medical digital radiography.

Another aspect of this application is to address, in whole or in part, at least the foregoing and other deficiencies in the related art.

It is another aspect of this application to provide, in whole or in part, at least the advantages described herein.

An aspect of this application is to provide methods and/or apparatus to address and/or reduce disadvantages caused by the use of radiography CT imaging apparatus and/or methods using the same.

An aspect of this application is to provide material identification or differentiation methods and/or apparatus, referred to herein as conditional likelihood method, that can employ the statistical independence of an image plurality (e.g., spectral absorption, absorption and phase shift (i.e., PCI), spectral PCI).

Another aspect of the application is to provide methods and/or apparatus embodiments for material identification or decomposition in CT medical imaging such as PCI CT, PCI spectral CT and/or absorption-based spectral CT. Another aspect of the application is to provide imaging methods and/or apparatus embodiments that can implement PCI CT scan results in at least two statistically independent reconstructions (e.g., slices) of identical area of an object. Another aspect of the application is to provide methods and/or apparatus embodiments that can provide likelihood methods and/or apparatus embodiments that can provide material identification individually for each reconstruction (e.g., slice) on pixel-by-pixel basis. One embodiment provide methods and/or apparatus embodiments for detuned phase contrast imaging to provide a phase shift image (e.g., projection image) for radiographic medical imaging.

In accordance with one embodiment, the present invention can provide a method executed at least in part on a computer, that can include obtaining a first plurality of 2D projection images over a range of scan angles, obtaining a second plurality of 2D projection images over a range of scan angles, generating at least two statistically independent reconstructed images of a portion of an object from the first plurality of 2D projection images and the second plurality of 2D projection images, determining a material property for each of at least two materials represented in the projection images, using a conditional likelihood determination comprising the material property for said each of at least two materials and the at least two statistically independent reconstructed images to differentiate the at least two materials as a function of volume in a reconstructed image of the portion of the object, and storing the reconstructed image of the portion of the object having the at least two materials differentiated in a computer-accessible memory.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 19 is a diagram that illustrates examples of the open field images measured in the detector plane for tuned and detuned configurations of related art phase contrast imaging systems.

DESCRIPTION OF EXEMPLARY EMBODIMENTS

Figure 1:
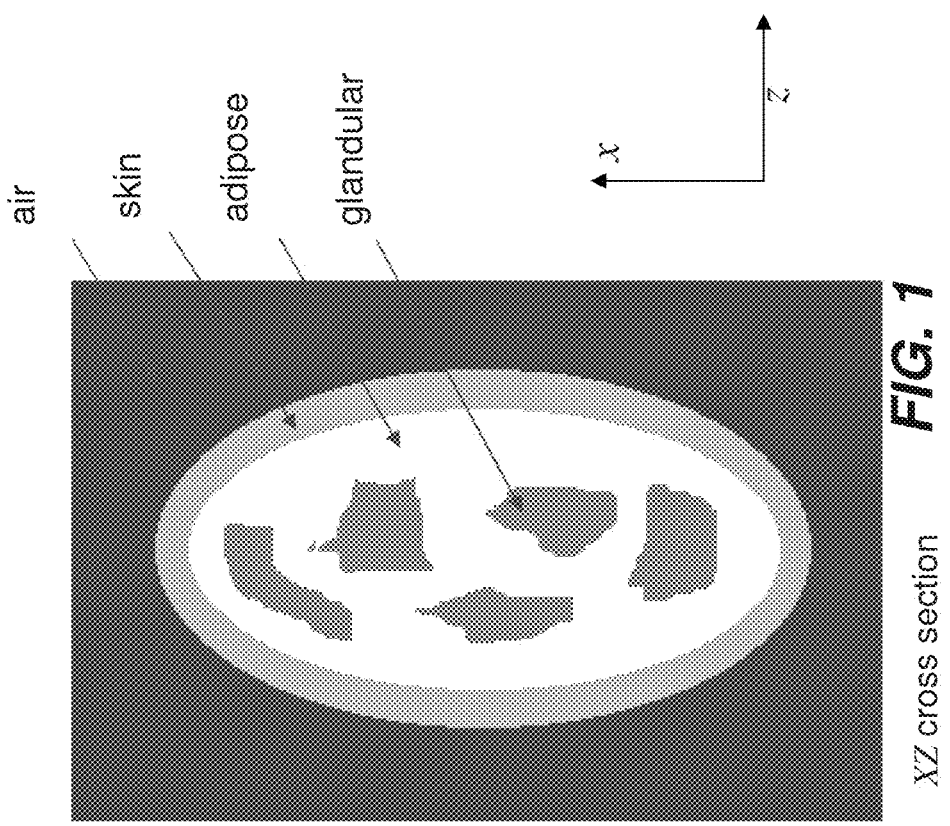
FIG. 1 is a diagram that shows an XZ cross section of a breast digital phantom.

The following is a description of exemplary embodiments of the invention, examples of which are illustrated in the accompanying drawings. Wherever possible, the same reference numbers will be used throughout the drawings to refer to the same or like parts.

For simplicity and illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention may have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Certain exemplary system and/or method embodiments described herein can provide the capability to differentiate materials using absorption and phase images from x-ray phase contrast CT scan. A PCI CT scan can result in two statistically independent volumetric images: 1) attenuation image, which is dependent on the absorption properties of the object, and 2) phase shift image characterized by the phase properties of the object. Such volumetric images can be represented by a series of cross sectional slices, where the measurements are expressed per unit of length (e.g., the attenuation image can be expressed in 1/cm units and phase shift image can have units of radians/cm). Embodiments herein can provide a likelihood method that can identify or differentiate materials individually for each slice on pixel-by-pixel basis. Alternatively, embodiments herein can provide a likelihood method/apparatus that can identify or differentiate materials individually for each reconstruction at more than one pixel at a time (e.g., binning, probability) to reduce computations or to take advantage of object and/or image characteristics (e.g., an adjacent pixel is likely to be the same material). Also, embodiments of the application can apply a likelihood method to spectral PCI CT data, where the absorption and phase information are obtained for different energy bins or different mean energies (e.g., using an energy resolving detector). In such a case, binned by energy data can also be considered as statistically independent.

A preferred or minimal number of statistically independent slice images (also referred to as datasets) used by embodiments herein (e.g., a likelihood method) is at least two. For example in a case of the PCI CT setup, a single x-ray scan can provide two independent datasets: 1) absorption and 2) phase shift. When spectral capabilities are added to PCI CT setup (e.g., energy-resolving detector is used, or two or more scans at different mean energies are performed), the number of independent datasets becomes higher than two, which can improve the material differentiation capabilities of embodiments herein. Further, the likelihood method embodiment can also be applied to conventional (e.g., absorption-based) spectral CT setup where an energy-resolving detector is used or several CT scans are acquired at different mean energies. Accordingly, method and/or system embodiments herein can be applied to a) phase contrast imaging CT, b) phase contrast imaging spectral CT, or c) conventional (absorption-based) spectral CT and the like.

Probability Density Function

Computed tomography can use measurements of line integrals through the imaged object at different angular positions. As a result of CT data reconstruction, the measurements can be expressed in units per unit of length. For example, the reconstruction of the PCI CT data can result in attenuation per unit of length (1/cm) and phase shift per unit of length (radians/cm). Both attenuation and phase shift are energy dependent. Such energy dependencies can be empirically found, for example, by imaging samples of materials with pure content (e.g., phantoms or biopsy/postmortem samples) at different energies of x-ray exposure. As described herein, these types of measurements will be referred to as calibration runs. When a histogram of an image of a sample of pure uniform material is taken (e.g., the calibration run is taken), the histogram results in a Poisson-like distribution, which at sufficient numbers of x-ray photons can be represented by Gaussian, Equation (2).

$$g(x) = \frac{1}{\sqrt{2\pi}\,\sigma} e^{-(x-x_c)^2/2\sigma^2}. \tag{2}$$

In equation (2), $x_c$ is the mean value of the distribution, $\sigma$ is the variance, and x is the measured value. The measurement x is energy dependent, which makes $x_c$ and $\sigma$ to be energy dependent. As a result of calibration runs, both parameters $x_c$ and $\sigma$ can be tabulated at different energies for different materials. The Gaussian distribution in equation (2) is presented in normalized form and will be referred to herein as a probability density function (pdf). However, embodiments of the application are not intended to be so limited, for example, other peak-like distribution, which fits the data well, can also be used. Further, since $\sigma$ can characterize the noise properties of the image and the noise can be dependent on x-ray fluence, $\sigma$ or noise can be tabulated at different x-ray exposure levels. When applying likelihood method/system embodiments to collected data or CT imaging, a calibration file with the same or closest level to that used during acquisition exposure can be utilized. This will address or assure that likelihood pdfs have the noise characteristics comparable to data of the imaged object. Alternatively, one or more closest exposure level calibration files, or two or more or two selected calibration files or the like can be interpolated to an acquisition exposure level.

Conditional Likelihood

A likelihood L is formed based on statistical independence of reconstructed CT datasets (e.g., images) and can be written as a normalized product of pdfs of different materials:

$$L_M = \frac{\prod\limits_{dataset} pdf_{dataset}^M}{\sum\limits_{M} \prod\limits_{dataset} pdf_{dataset}^M}. \tag{3}$$

In equation (3), M can refer to material, and subscript dataset can denote the measurement (e.g., absorption or phase shift) reconstructed from CT data. For example in case of the PCI CT acquired in a single scan, two datasets, attenuation μ and phase shift φ, can be measured and the product over dataset yields:

$$\prod\limits_{dataset} pdf_{dataset}^M = pdf_\mu^M \cdot pdf_\varphi^M.$$

In the case that the PCI CT is performed twice at different mean energies of x-ray spectra, the number of datasets doubles, e.g., $\mu_1$ and $\phi_1$, and $\mu_2$ and $\phi_2$ (the subscripts refer to scan number). The same condition can be true for PCI CT using an energy-resolving detector, (e.g., instead of separate scans a single scan can provide similar (e.g., two) spectral data). The spectral data is also statistically independent. Thus, when spectral data contains n energy bins (or n scans at different energies), then the product over dataset becomes:

$$\prod\limits_{dataset} pdf_{dataset}^M = \prod\limits_n \left( pdf_{\mu\_bin\_n}^M \cdot pdf_{\varphi\_bin\_n}^M \right).$$

The same approach can be valid for absorption-based spectral CT, where attenuation only is measured at different energies. For such a case the expression for the product can be simplified to:

$$\prod\limits_{dataset} pdf_{dataset}^M = \prod\limits_n pdf_\mu^M.$$

The likelihood values can be composed according to equation (3) on pixel-by-pixel basis for each material selected or intended for identification. The values of likelihood can be normalized, e.g., the summation over all materials yields one. Further, the pixel (ij) can be assigned with the material that has a desired or the highest likelihood value at the pixel, e.g., $$\text{Material}^{ij}(M) = \max(L_M^{ij}). \tag{4}$$

Once determined, the likelihood value at the pixel can be presented in various ways. For example, the binary format (0 or 1) can be used to show images of identified materials filled with 0 s in the pixels where the material is not identified and with 1 s in the pixels where the material is found (in other words images would have a Boolean type of data). Alternatively, the pixels with identified materials can be filled with the corresponding value of the CT measurement (e.g., attenuation, phase shift, and etc.). Alternatively, the result can be saved in a single image that contains $\max(L_M)$ values or individually saved as image for each material with the corresponding $L_M$ value.

Simulations

Although, exemplary conditional likelihood material identification embodiments described herein can be applied to any medical imaging application where material differentiation is needed, one exemplary embodiment will now be described where the application is a breast CT.

Modeling of Absorption and Phase Shift in the Materials

Again, in x-ray technology, the refractive index n of a material can be expressed by a complex number:

$$n = 1 - \delta + \beta, \quad (1)$$

where the imaginary part $\beta$ contributes to the attenuation of the amplitude and the real part $\delta$ (refraction index decrement) is responsible for the phase shift. When the x-ray is passing through the tissue or object, the attenuation and phase shift can be calculated as:

$$\begin{cases} \mu(x, y) = \frac{4\pi}{\lambda} \int \beta(x, y, z) dz \\ \varphi(x, y) = \frac{2\pi}{\lambda} \int \delta(x, y, z) dz. \end{cases} \quad (5)$$

For a compound of density $\rho$ the refractive index can be expressed in terms of the atomic scattering factors $f_1$ and $f_2$:

$$n \cong 1 - \frac{r_e N_a \lambda^2 \rho}{2\pi} \left( \sum_k x_k (f_{1,k} + i f_{2,k}) \right) / \left( \sum_k x_k A_k \right), \quad (6)$$

where $r_e$, $N_a$, $\lambda$, and $\rho$ are the electron radius, Avogadro number, photon wavelength, and effective density of compound, respectively. The summation is taken over the relative concentrations $x_k$ of each of the chemical elements of atomic mass $A_k$ comprising the compound.

Geometry and Parameters of CT Simulation

A simulation was conducted for single slice parallel beam geometry CT. As described herein, scatter and beam hardening effects were not taken into account, however, such effects and other effects can be addressed using various techniques known to one skilled it the art. The x-ray spectrum was generated at a given kVp value (e.g., 40 kVp) with a given exposure value, and the digital phantom of the breast was used to model absorption and phase change experienced by traversing x-ray beam.

Digital Phantom

The breast is primarily composed of two types of tissue: glandular and adipose. Additionally, a thin layer of skin surrounds the breast. The digital phantom shown in FIG. 1 models the cross section of a compressed breast including three materials: 1) skin, 2) adipose tissue, and 3) glandular tissue. The background in the image was assumed to be air.

Each of the materials shown in FIG. 1 was assigned a particular code value. Using equation (6), the XZ cross sectional images of breast's $\beta$ and $\delta$ ("map" images) were generated. Then, the "map" images were substituted in equation (5) to get the line integrals along the direction of the x-ray beam propagation (i.e., z axis). The sinogram data was generated for 360 projection angles. Further, Poisson noise was added to both attenuation and phase shift sinograms to simulate the statistical fluctuations in the measurement for the 360 projection angles. Furthermore, a conventional filtered back projection algorithm was applied to obtain the XZ cross section of the breast.

The simulations were conducted for: a) single scan PCI CT, b) spectral PCI CT (with energy-resolving detector), and c) absorption-based spectral CT (with energy-resolving detector). In addition, the capability for identification of a cancerous tumor in the breast was demonstrated by simulation for a case of single scan PCI CT (although embodiments herein can be performed in spectral CT as well).

Calibration

Figure 2:
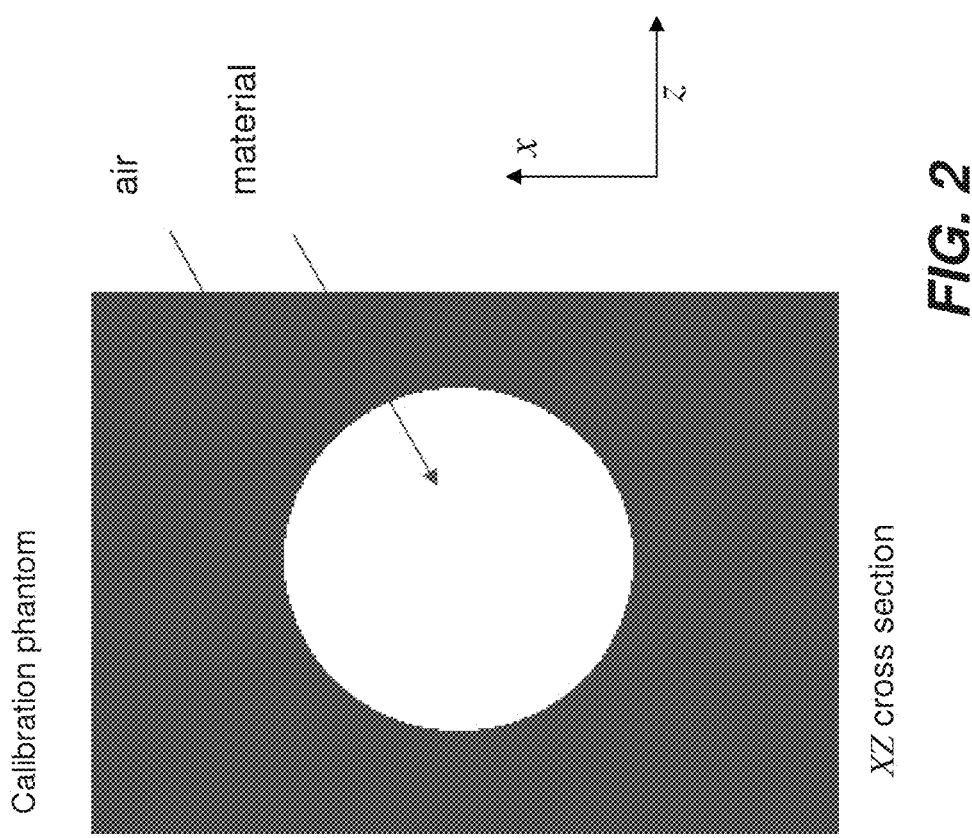
FIG. 2 is a diagram that illustrates an XZ cross section of an exemplary material calibration object or phantom.

FIG. 2 is a diagram that shows an XZ cross section of an exemplary material calibration phantom according to the application. As shown in FIG. 2, the calibration phantom was used to obtain the attenuation and phase shift probability density functions for each material (e.g., one or more materials). Thus, calibration runs or scans were performed for each material (e.g., air, skin, adipose, and glandular) with the same x-ray spectrum (e.g., kVp and exposure values) as used in simulation of breast CT scan.

Single Scan PCI CT

Figure 3:
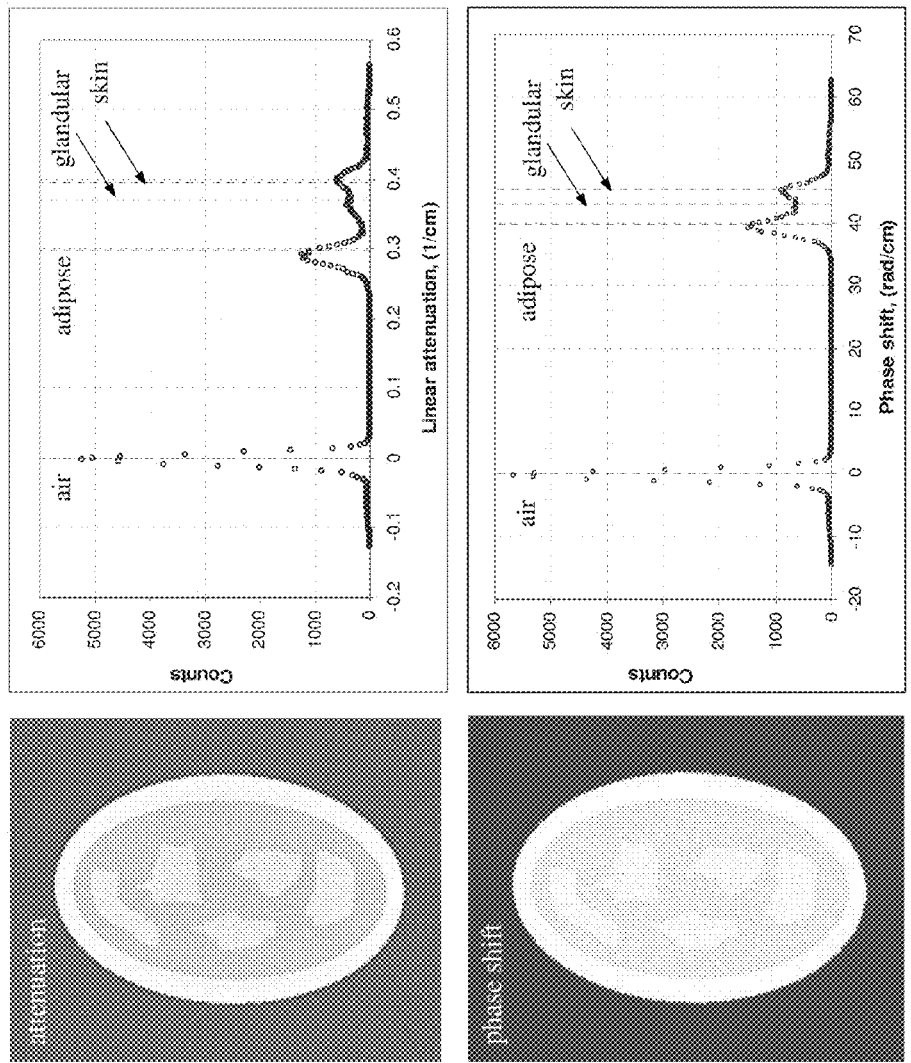
FIG. 3 is a diagram that illustrates a single PCI CT scan of the breast including linear attenuation image with its histogram to the right above a phase shift image with its histogram to the right on the bottom according to the application.

FIG. 3 is a diagram that shows exemplary results of single PCI CT scan of the breast where a linear attenuation image is on top and a phase shift image is on the bottom. As shown in FIG. 3, histograms of the images are shown to the right side of the images where dashed lines represent the expectation values of Gaussian pdfs of different materials in the histograms. The single scan PCI CT results in cross section images of attenuation and phase shift per unit of length. As shown in FIG. 3, the histograms contain several peaks, where each peak can correspond to one or more materials. Some of the peak's centers are slightly offset from the material calibration values. This slight offset can be caused by the overlap of Gaussian shaped distributions of materials, which effectively "push" the peaks away from each other.

Figure 4:
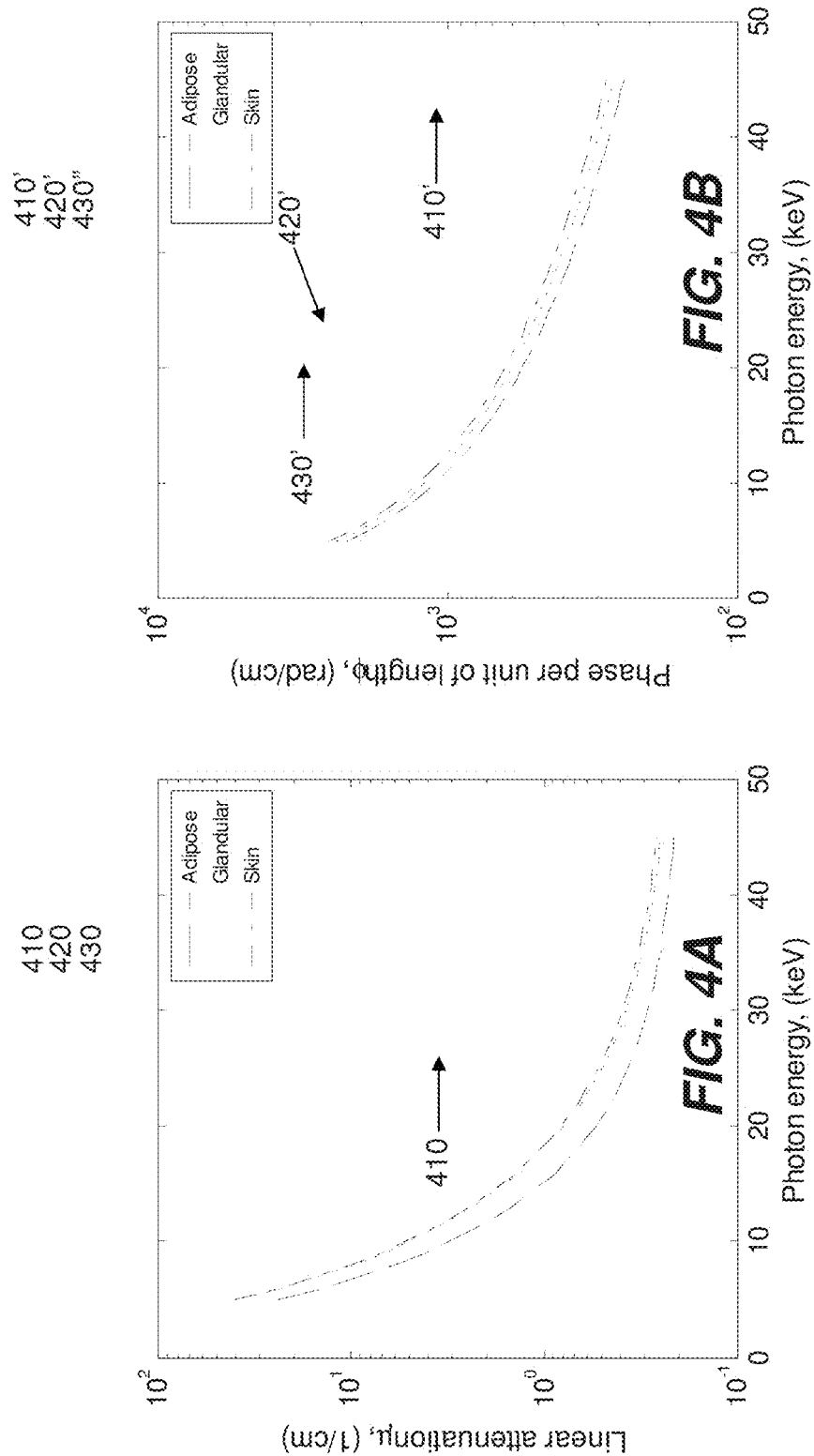
FIGS. 4A-4B are diagrams that illustrate respective plots for linear attenuation and phase shift per unit of length for exemplary tissues.

Also, the attenuation and phase shift values for glandular tissue and skin are close to each other. When a standard material differentiation approach is used (e.g., applying restrictive cuts to histograms), it might be unfeasible to separate between glandular and skin tissues. This difficulty or inability of standard material differentiation approach to differentiate similar materials such as glandular tissue and skin is supported by FIG. 4, which shows simulated attenuation and phase shift of breast components (i.e. linear attenuation plots for adipose tissue 410, glandular tissue 420, and skin tissue 430 and phase shift per unit of length plots for adipose tissue 410', glandular tissue 420', and skin tissue 430') as a function of photon energy. As shown in FIG. 4, glandular and skin tissues have very similar attenuation and phase shift curves for all energy ranges, which will result in histogram distributions with close to each other mean values.

Figure 5:
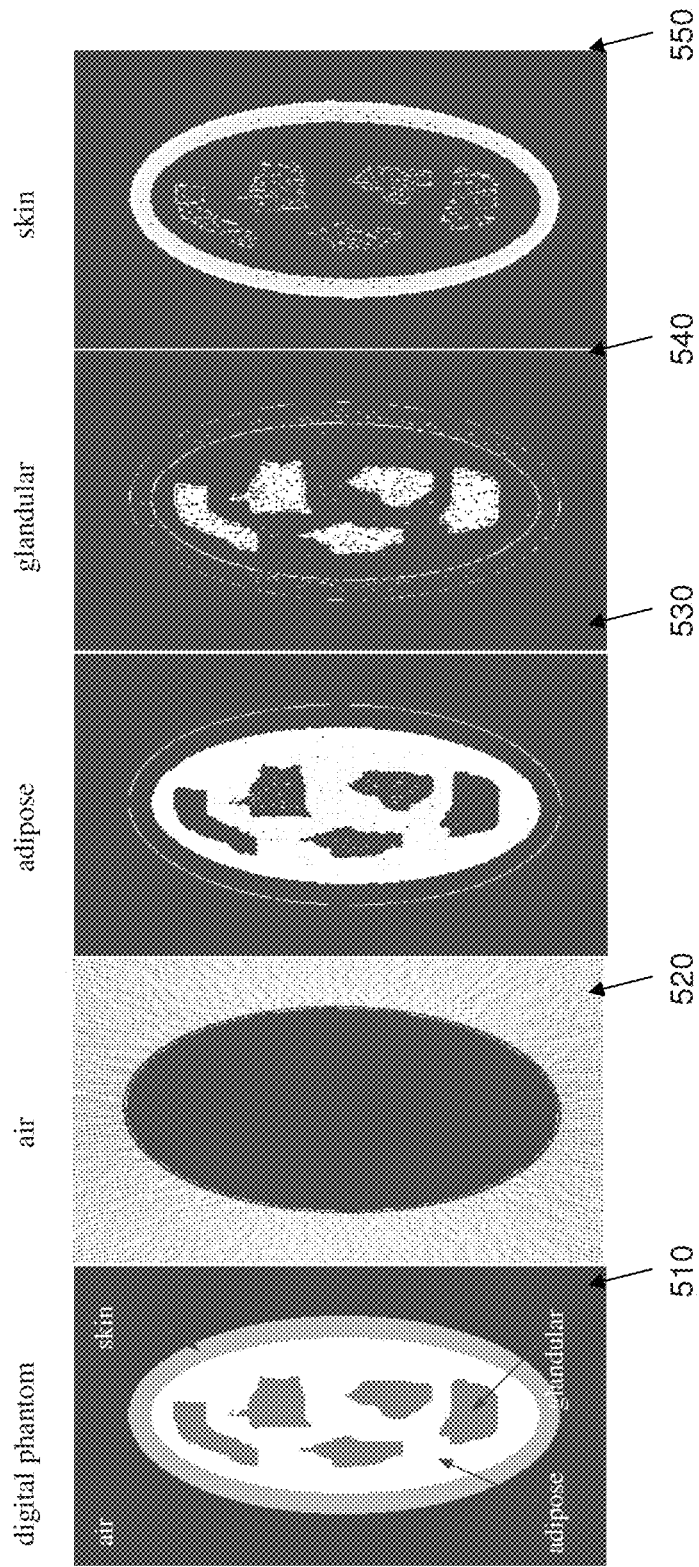
FIG. 5 is a diagram that illustrates exemplary results of four-material identification using a conditional likelihood method embodiment for a single PCI CT scan according to the application.

FIG. 5 is a diagram that illustrates exemplary results of four-material identification using a conditional likelihood embodiment for a single PCI CT scan (e.g., two statistically independent data sets: attenuation $\mu$ and phase shift $\phi$) according to the application. The materials were assigned according to Equation (4). As shown in FIG. 5, a first image 510 shows the digital phantom used in simulation. Then, a second image 520 shows materials identified as air in the cross-section followed by the images of identified adipose 530, glandular 540, and skin 550. The code values assigned to the images shown in FIG. 5 are linear attenuation values; however, embodiments according to the application are not intended to be so limited. For example, images with phase shift values can be generated, or the images can be assigned their corresponding CT values or Hounsfield units (HU).

Figure 6:
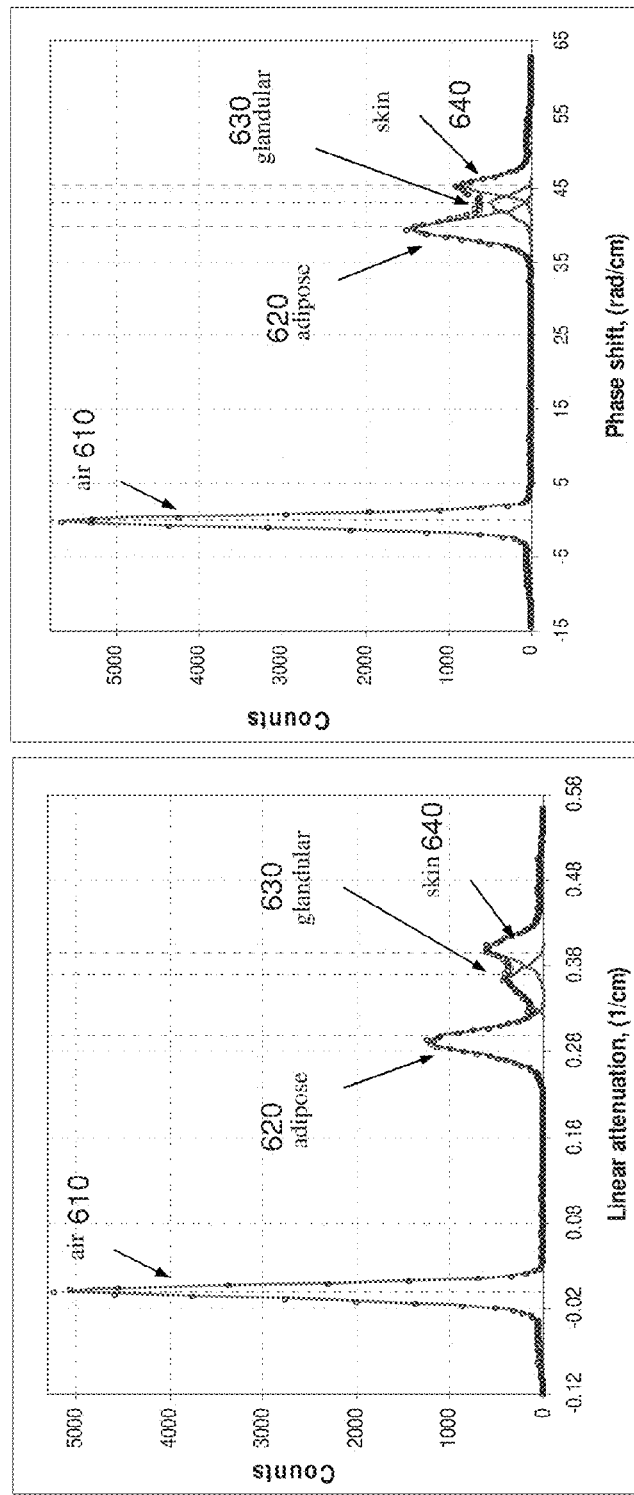
FIG. 6 is a diagram that illustrates superimposed histograms of identified materials for linear attenuation (left) and for phase shift (right) for a single PCI CT scan according to an embodiment of the application.

FIG. 6 is a diagram that shows superimposed histograms of identified materials for linear attenuation (left) and for phase shift (right). Solid lines represent materials and circle points belong to scanned breast image. As shown in FIG. 6, peaks occur for identified materials air 640, adipose tissue 610, glandular tissue 620, and skin tissue 630. The vertical dashed lines in FIG. 6 are the expectation values of corresponding Gaussian pdfs.

Spectral PCI CT

When the spectral information is available for embodiments of imaging systems and/or methods according to the application, material identification can improve. Thus, when the spectral information is available for a PCI CT imaging method embodiment, the identification capabilities can be increased. In case of two energy bins (e.g., in an energy resolving detector), the number of statistically independent datasets doubles (e.g., from two to four).

Figure 7:
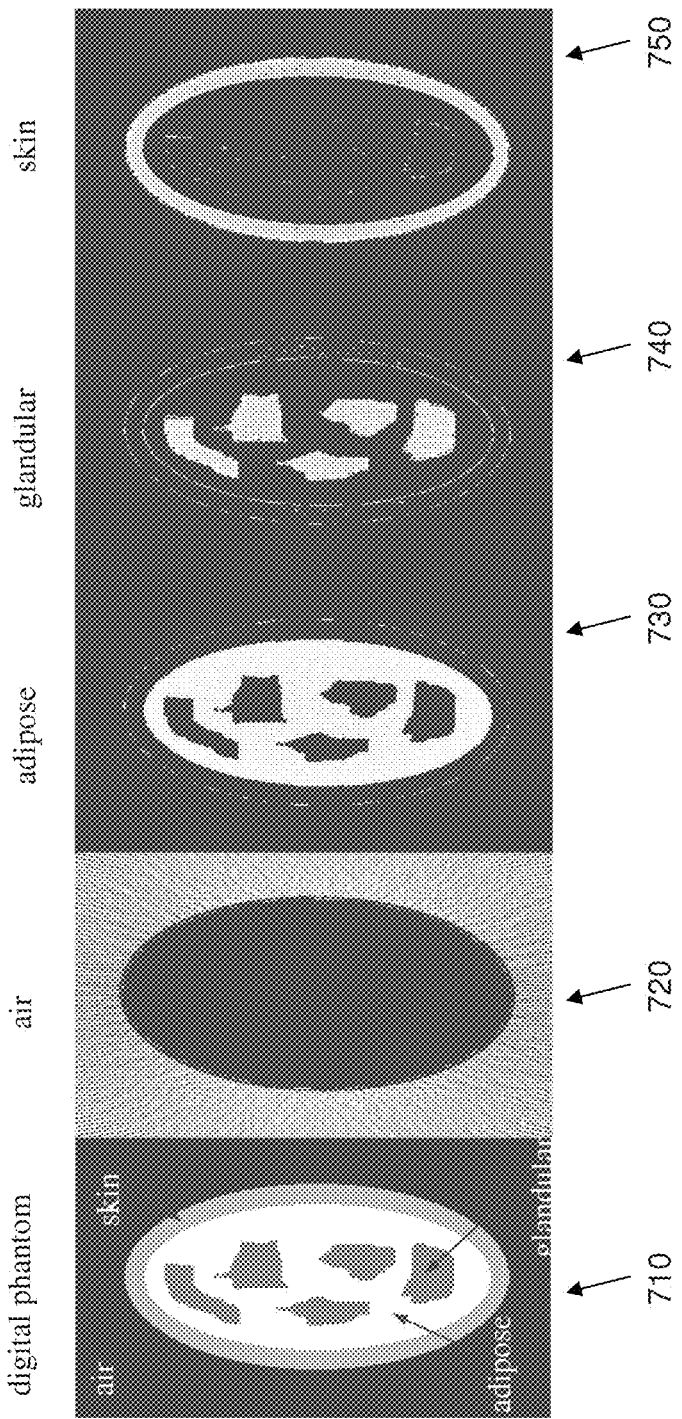
FIG. 7 is a diagram that illustrates exemplary results of four-material identification using another conditional likelihood method embodiment for a spectral PCI CT scan according to the application.

FIG. 7 is a diagram that illustrates exemplary results of four-material identification using another conditional likelihood embodiment for a spectral PCI CT scan according to the application. FIG. 7 shows the results of four-material identification performed with conditional likelihood embodiment using the condition in Equation (4) (e.g., four statistically independent data sets: attenuation $\mu$ and phase shift $\phi$ at two different energy levels). As shown in FIG. 7, a first image 710 shows the digital phantom used in simulation and images of likelihood material identified as air 720, adipose 730, glandular 740, and skin 750 follow. The differentiation between glandular and skin tissues is significantly improved in comparison to a single PCI CT scan.

Figure 8:
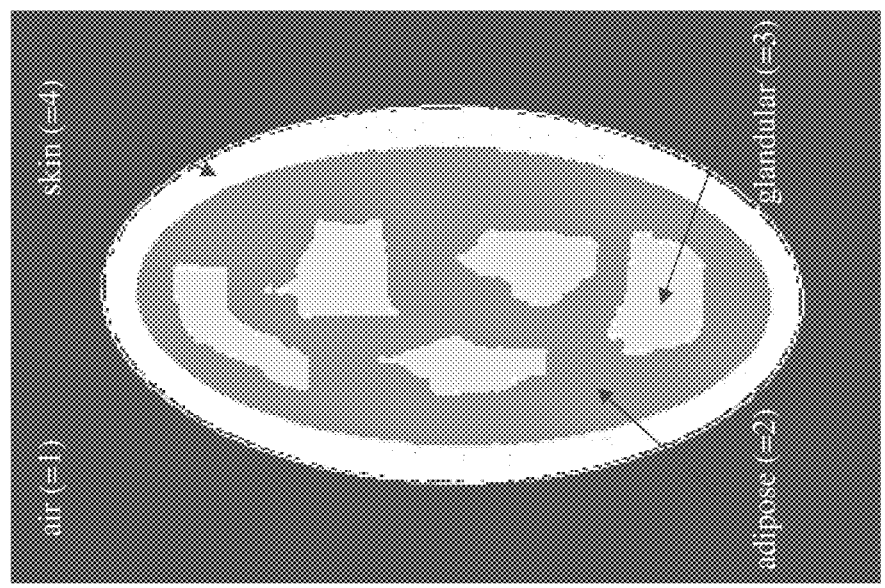
FIG. 8 is a diagram that illustrates exemplary results of four material identification of FIG. 7 presented in alternative code values.

In the PCI CT imaging method spectral information embodiment, two energy bins were setup up as: $bin_1 \in [10, 29]$ and $bin_2 \in [30, 50]$. The code values shown in FIG. 7 images were set to be equal to the linear attenuation of the first energy bin. As described herein, the code values in images of identified materials can be assigned differently, for example the code values can be set to be equal to attenuation values of second bin or to the phase values of first bin, second bin, and/or their sum, or other combination known to one skilled in the art. Alternatively, exemplary results can be presented as an image of likelihood values, namely $\max(L_m)$ as shown in FIG. 8.

Absorption-based Spectral CT

Figure 9:
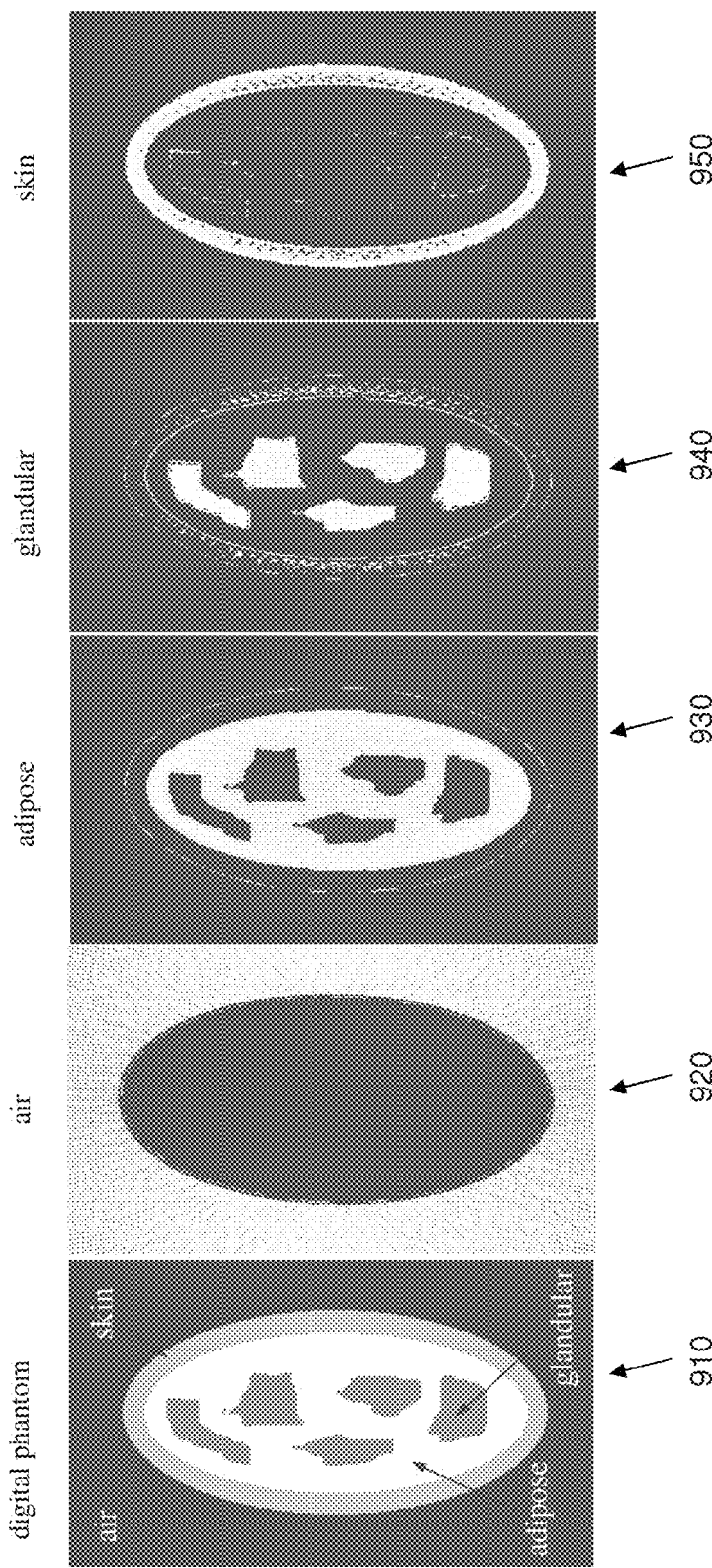
FIG. 9 is a diagram that illustrates exemplary results of four-material identification using yet another conditional likelihood method embodiment for conventional (absorption based) CT according to the application.

As described earlier, embodiments of likelihood methods can be applied to conventional (absorption-based) CT, where two or more runs at different photon energy are acquired, or an energy-resolving detector can be used (e.g., spectral content is available) in a single run. FIG. 9 shows the results of four-material decomposition for single scan absorption-based CT model with two-bin energy resolving detector. As shown in FIG. 9, a first image 910 shows the digital phantom used in simulation and images of likelihood material identified as air 920, adipose 930, glandular 940, and skin 950 follow. The material identification shown in FIG. 9 is similar to results obtained in single scan PCI CT simulation, where glandular and skin tissues are identified with mutual contaminations (e.g., some areas of skin are identified as glandular tissue and contrariwise). An increase in a number of energy bins can improve the material differentiation, for example, where four instead of two datasets can be used.

Identification of Tumor in the Breast

Figure 10:
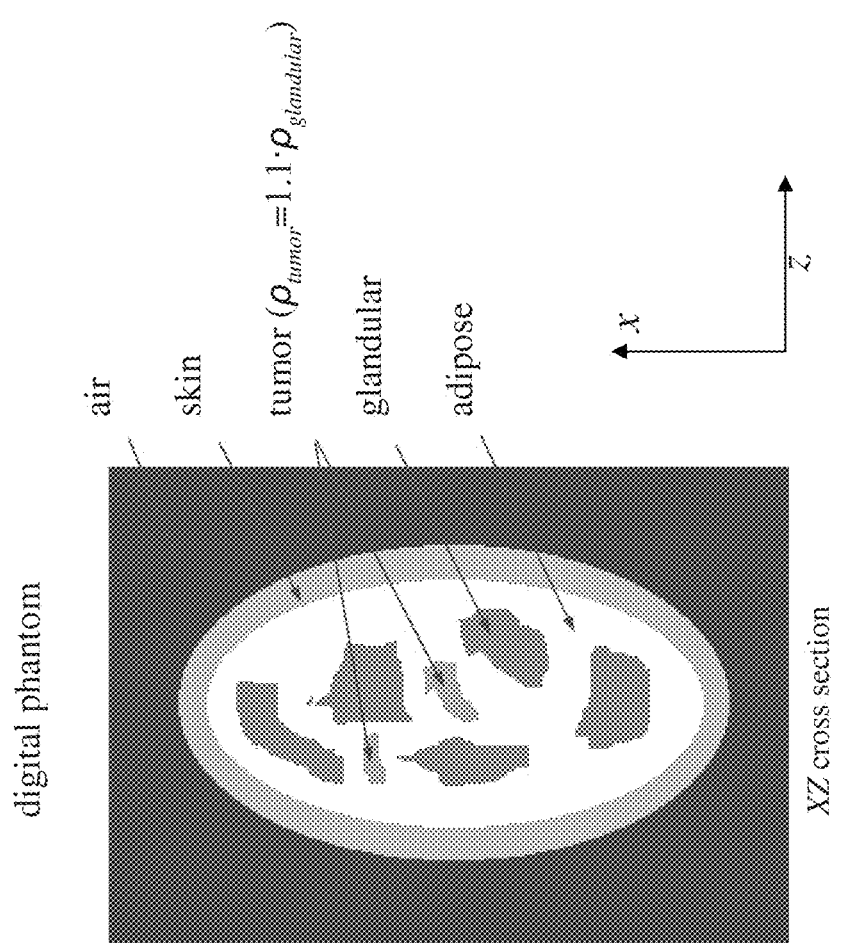
FIG. 10 is a diagram that illustrates an XZ cross section of another exemplary digital phantom of the object, which contains air, adipose tissue, glandular tissue, skin, and glandular-based tumor with 10% higher density than glandular tissue.

The simulations using a digital phantom of the breast described herein showed the feasibility of material identification with conditional likelihood system and/or method embodiments. The materials with close attenuation and/or phase shift values (for example, glandular and skin tissues), which almost cannot be differentiated by traditional hard cuts applied to image histogram, were individually or successfully identified by likelihood method embodiments. Next, the capability of conditional likelihood system and/or method embodiments to identify additional materials like abnormalities such as a tumor can be demonstrated. In one example, exemplary embodiments can be used to identify a tumor material that has the same chemical structure as glandular tissue except of the density, which is set to be higher than glandular by 10% (as an example). An XZ cross section of an exemplary breast digital phantom that contains air, adipose, glandular, skin, and tumor tissues is shown in FIG. 10.

The level of the noise in reconstructed CT images or projection images obtained in a CT scan is dependent on the x-ray fluence. In one simulation shown in FIG. 11, the entrance air-kerma at the surface of the breast was set to ~25 µGy. This x-ray fluence level can test a material identification embodiment in a low dose and high noise situation. In this case, calibration runs or scans were conducted using the digital phantom shown in FIG. 2 for all the tissues, including the tumor tissues.

Figure 11:
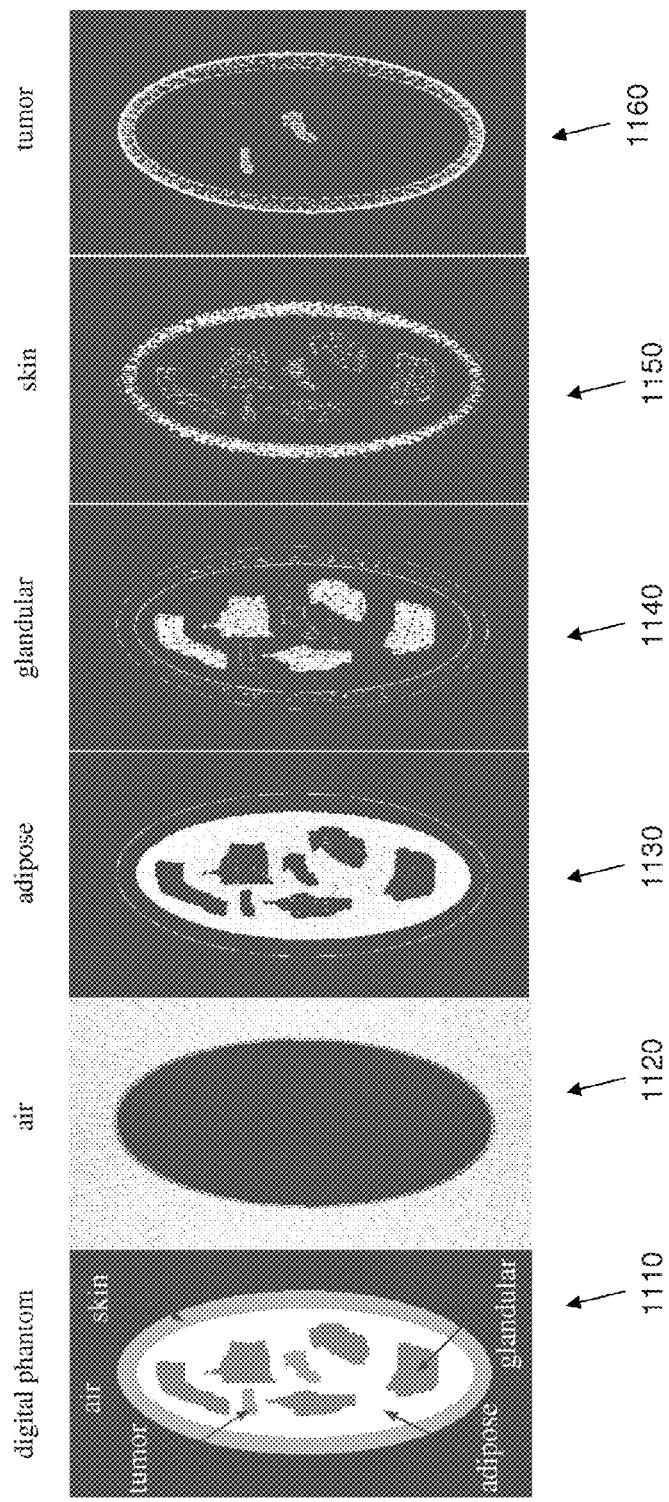
FIG. 11 is a diagram that illustrates exemplary results of five-material identification using a conditional likelihood method embodiment for a single PCI CT scan at air-kerma of approximately 25 µGy according to the application.

FIG. 11 is a diagram that illustrates exemplary results of five-material identification using a conditional likelihood embodiment for a single PCI CT scan according to the application. The first image 1110 in FIG. 11 shows the digital phantom used in simulation. The rest, are the images of materials identified as air 1120, adipose 1130, glandular 1140, skin 1150, and tumor 1160, respectively.

Identification of the tumor mass by the conditional likelihood embodiment is clearly shown in FIG. 11, however some contamination from skin and CT reconstruction artifacts (e.g., that contribute to the bright ring around the breast) are present in the image of tumor. The plots are shown in units of linear attenuation, although similar histograms can be plotted for phase shifts.

Figure 12:
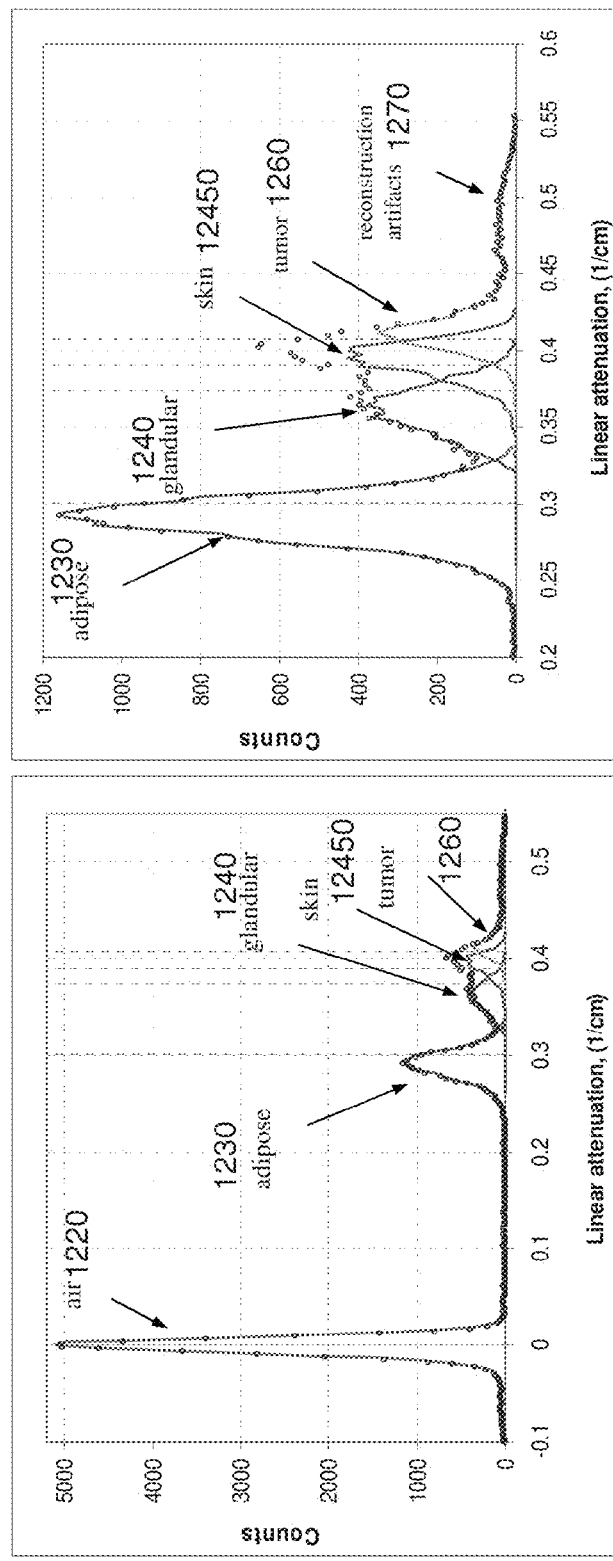
FIG. 12 is a diagram that illustrates superimposed histograms of identified materials for linear attenuation (left) and for phase shift (right) according to an embodiment of the application shown in FIG. 11.

FIG. 12 is a diagram that shows superimposed histograms of identified materials for linear attenuation (left) showing all materials, including air and histograms for phase shift (right) showing only materials other than air. Thus, the phase shift histogram shown in FIG. 12 zooms in on the identified non-air materials. Solid lines represent materials and circle points belong to scanned breast image. As shown in FIG. 12, peaks occur for identified materials air 1220, adipose tissue 1230, glandular tissue 1240, skin tissue 1250 and tumor tissue 1260. The vertical dashed lines in FIG. 12 are the expectation values of corresponding Gaussian pdfs.

In the current simulation for breast CT imaging, the glandular, skin, and tumor are the most difficult to differentiate materials, due to a strong overlap of their respective distributions. Thus, the neighboring distributions in particular have mutual contaminations, such as image of the skin shows glandular and tumor tissue, and image of tumor has contamination from skin. Cross contaminations between glandular and tumor tissues are almost not present since their distributions are significantly separated. Further, as shown in FIG. 12, the histogram of tumor image contains a reconstruction artifacts peak 1270 on the right hand side. According to embodiments of the application, such contamination can be removed by placing a hard cut on the histogram. Alternatively, the reconstruction artifacts can be modeled with a pdf and then identified as a separate material using likelihood routine to remove or reduce the reconstruction artifacts peak 1270.

Figure 13:
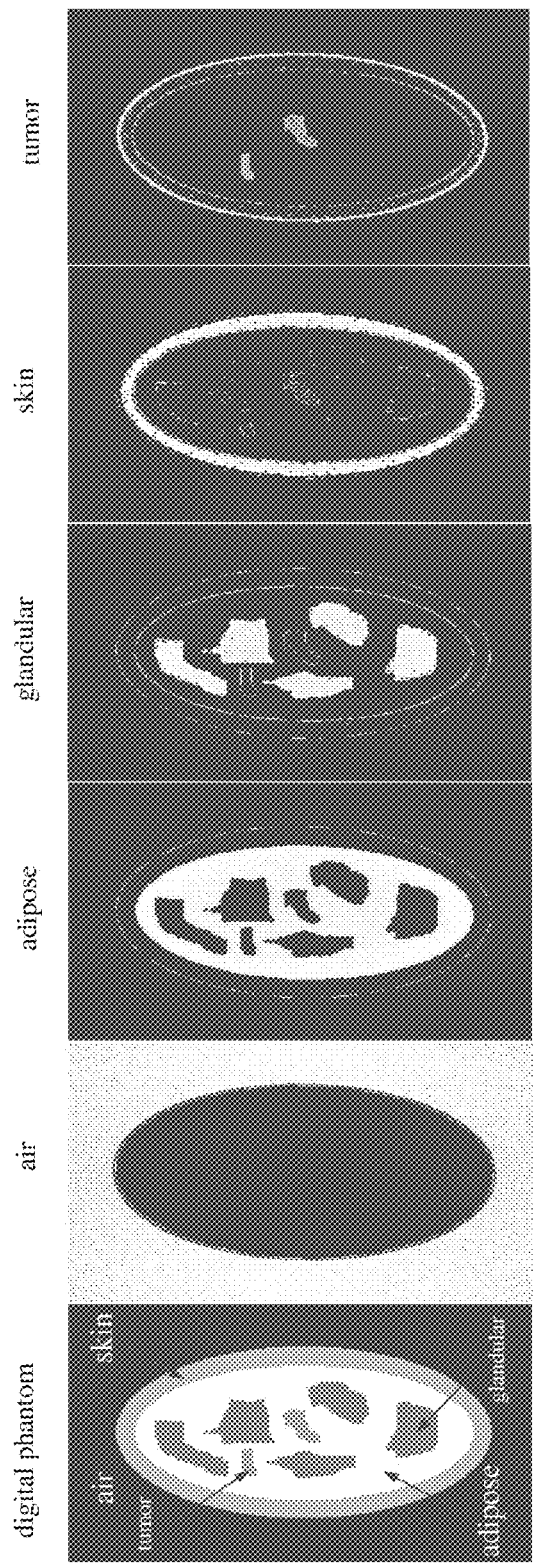
FIG. 13 is a diagram that illustrates exemplary results of five-material identification using conditional likelihood embodiment in a case of a single scan PCI CT scan at air-kerma of approximately 250 µGy according to the application.
Figure 14:
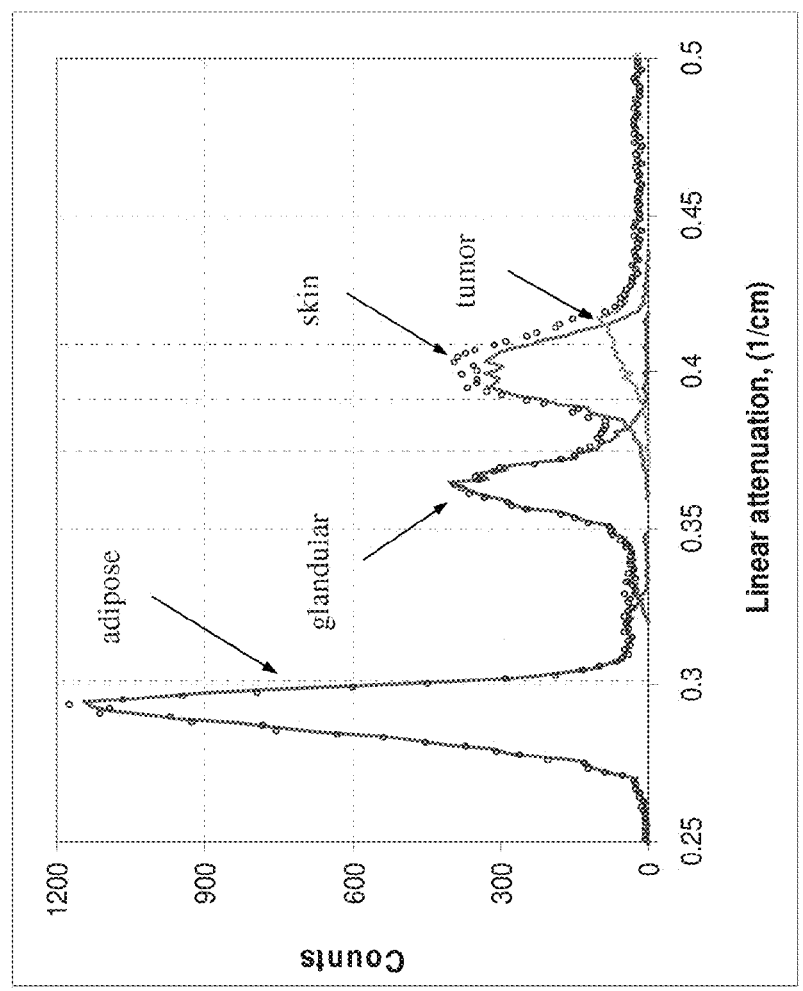
FIG. 14 is a diagram that illustrates superimposed histograms of differentiated tissues in linear attenuation units according to an embodiment of the application shown in FIG. 13.

A major reason for a high cross contamination among glandular, skin, and tumor is low level of exposure in the embodiment of FIGS. 11-12. When the photon flux is increased, the noise levels reduce and standard deviations of material pdfs become smaller (e.g., the pdfs get narrower). This higher level of exposure can reduce the overlap between material distributions and therefore can improve the identification. Also, the materials can be differentiated better when spectral capabilities are added to PCI CT configuration. FIG. 13 shows material differentiation for single PCI CT embodiment scan using 10 times higher exposure than in FIG. 11 (e.g., ~250 µGy). FIG. 14 shows the histograms for adipose, glandular, skin, and tumor tissues.

As shown in FIGS. 13-14, cross contaminations between glandular and skin, and skin and tumor can be significantly reduced. As shown in FIG. 14, the fractional content of the tumor is significantly smaller than in previous case (FIG. 12). The modeled in the digital phantom ratio of tumor mass to skin tissue was in the order or 6/100. FIG. 12 showed the ratio being equal approximately 44/100, while in case of higher dose the ratio changed to 20/100.

CT Apparatus

Computed tomography (CT) imaging apparatus and imaging algorithms used to obtain 3-D volume images using such systems are well known in the diagnostic imaging art and are, therefore, not described in detail in the present application.

In typical applications, a computer or other type of dedicated logic processor for obtaining, processing, and storing image data is part of the CT system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the present application.

Figure 15:
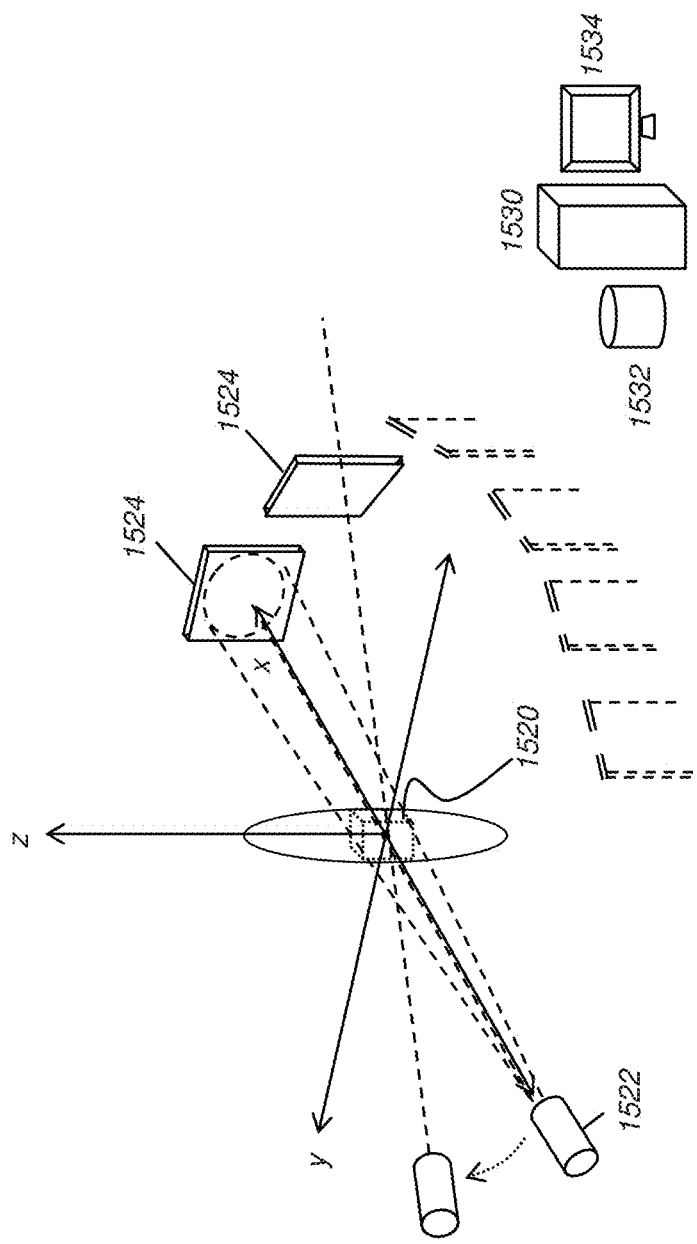
FIG. 15 is a schematic diagram showing components and architecture used for conventional CT scanning.

Referring to the perspective view of FIG. 15, there is shown, in schematic form and using exaggerated distances for clarity of description, the activity of an exemplary conventional CT imaging apparatus for obtaining the individual 2-D images that are used to form a 3-D volume image. A radiation source 1522 directs radiation through a beam shaping apparatus (not shown) toward a subject 1520, such as a patient or other imaged subject. A sequence of images of subject 1520 is obtained in rapid succession at varying angles about the subject over a range of scan angles, such as one image at each 1-degree angle increment in a 360-degree orbit. A DR detector 1524 is moved to different imaging positions about subject 1520 in concert with corresponding movement of radiation source 1522. For example, such corresponding movement can have a prescribed 2D or 3D relationship. FIG. 15 shows a representative sampling of DR detector 1524 positions to illustrate how these images are obtained relative to the position of subject 1520. Once the needed 2-D projection images are captured in a prescribed sequence, a suitable imaging algorithm, such as FDK filtered back projection or other conventional technique, can be used for generating the 3-D volume image. Image acquisition and program execution are performed by a computer 1530 or by a networked group of computers 1530 that are in image data communication with DR detectors 1524. Image processing and storage is performed using a computer-accessible memory in image data communication with DR detectors 1524 such as computer-accessible memory 1532. The 3-D volume image or exemplary 2-D image data can be presented on a display 1534.

Figure 16:
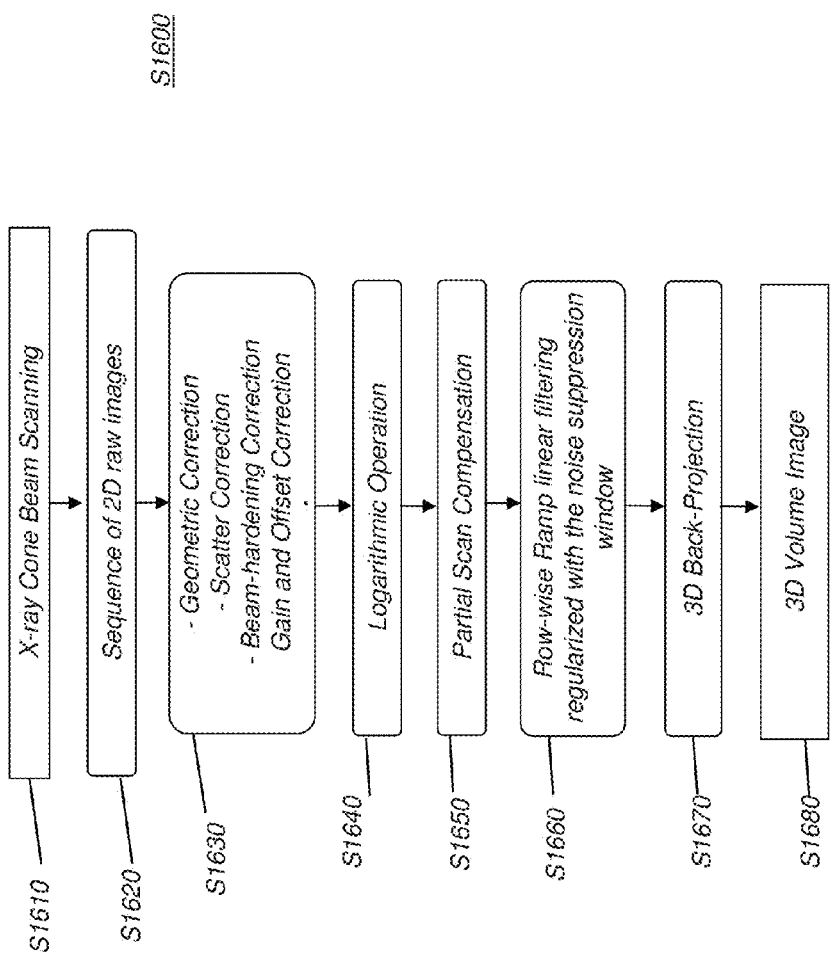
FIG. 16 is a logic flow diagram showing the sequence of processes used for conventional CT volume image reconstruction.

The logic flow diagram of FIG. 16 shows a conventional image processing sequence S1600 for CT reconstruction using partial scans. A scanning step S1610 directs cone beam exposure toward the subject, enabling collection of a sequence of 2-D raw data images for projection over a range of angles in an image data acquisition step S1620. An image correction step S1630 then performs standard processing of the projection images such as but not limited to geometric correction, scatter correction, gain and offset correction, and beam hardening correction. A logarithmic operation step S1640 obtains the line integral data that is used for conventional reconstruction methods, such as the FDK method well-known to those skilled in the volume image reconstruction arts.

An optional partial scan compensation step S1650 is then executed when it is necessary to correct for constrained scan data or image truncation and related problems that relate to positioning the detector about the imaged subject throughout the scan orbit. Optional step S1650 can be used for cone beam (CB) CT where typically a limited or partial angular scan (e.g., 220-degrees or 180-degrees plus fan angle) can be used. A ramp filtering step S1660 follows, providing row-wise linear filtering that is regularized with the noise suppression window in conventional processing. A back projection step S1670 is then executed and an image formation step S1680 reconstructs the 3-D volume image using one or more of the non-truncation corrected images. FDK processing generally encompasses the procedures of steps S1660 and S1670. The reconstructed 3-D image can then be stored in a computer-accessible memory and displayed.

In the context of the present disclosure, the term "code value" can refer to the value that is associated with each volume image data element or voxel in the reconstructed 3-D volume image. The code values for CT images are often, but not always, expressed in Hounsfield units (HU).

Figure 17:
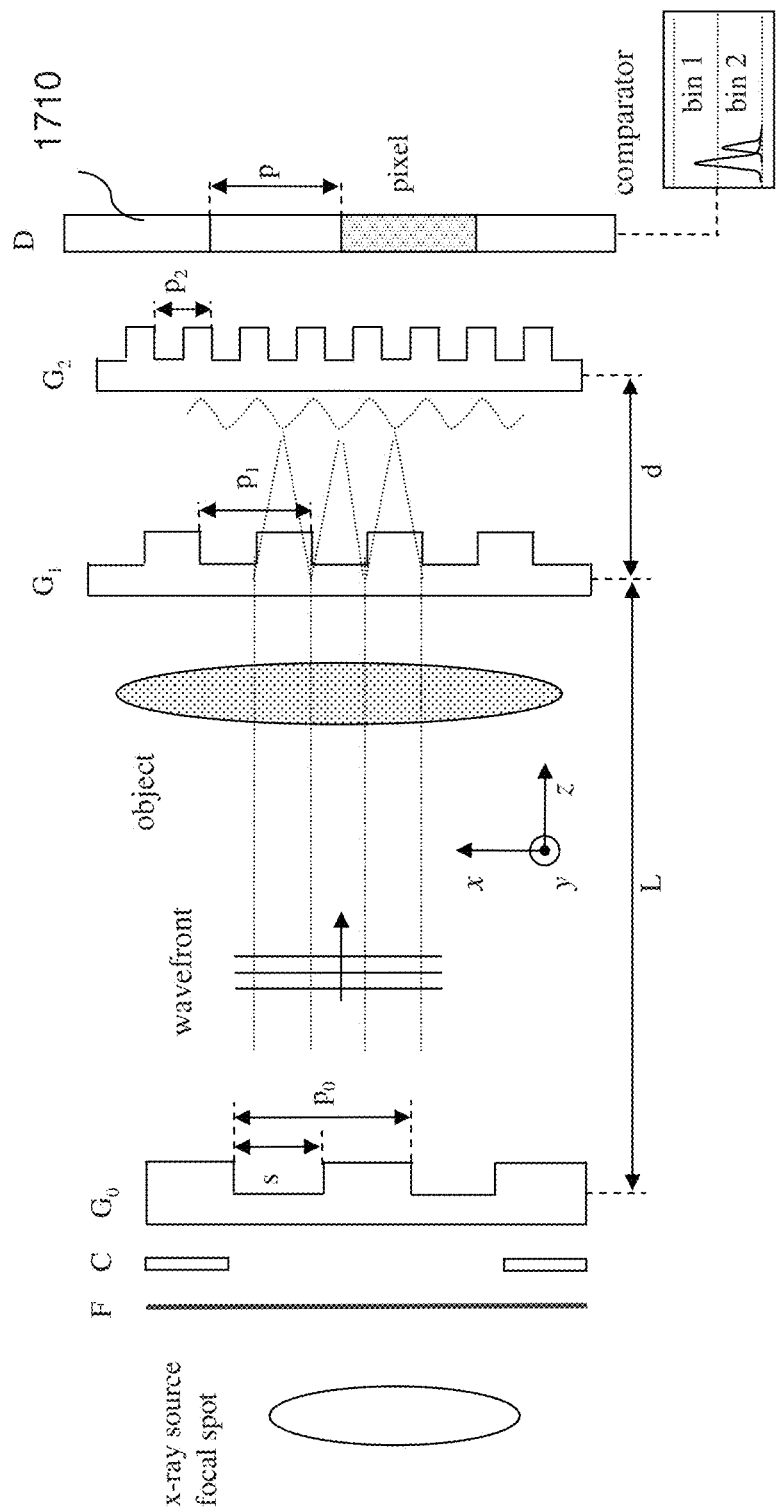
FIG. 17 is a diagram that shows a related art grating based PCI system using an energy resolving detector.

FIG. 17 is a diagram that shows an embodiment of a grating-based phase contrast imaging system using an energy-resolving detector. As shown in FIG. 17, an embodiment of a grating-based phase contrast imaging system can include a three-grating (G0, G1, G2) Talbot-Lau interferometer setup and an energy-resolving detector (e.g., photon-counting energy-resolving Cd—Zn—Te detector) 1710 placed behind an analyzer G2 grating. In one embodiment, an energy comparator in an imaging array or pixel of a detector (e.g., pulse height analysis) can allow energy discrimination.

Two exemplary system and/or method embodiments to implement dual energy or spectral imaging in phase contrast imaging respectively include a first embodiment using two x-ray exposures at different exposures (e.g., kVp values) and a second embodiment including only one x-ray exposure while using (at least) a two-bin energy-resolving detector.

Certain exemplary embodiments for slot-scanning phase-contrast digital imaging systems and/or methods for using the same can employ step-dither-step approaches, where one of the gratings, either phase grating G1 or analyzer grating G2, can be stepped with respect to another. For example, when moving analyzer grating G2 where N is a number of steps (e.g., using a piezo translational stage) required to cover a period of grating G2, and the lateral size of the grating G2 is $l_{G2}$; then the scan of an object with lateral size S can use or require $S/l_{G2} \cdot N$ of x-ray exposures. For an exemplary S=20 cm breast and 8 phase steps for a 1 cm wide G2 grating at each position (or slice) of the swing arm, then 20/1·8=160 x-ray exposures are used to scan the whole object. Note that $S/l_{G2} \cdot N$ can be considered a sufficient or minimal number needed for a full scan. To properly stitch the slices into an image of the whole object, slight overlaps between slices can be required.

Figure 18:
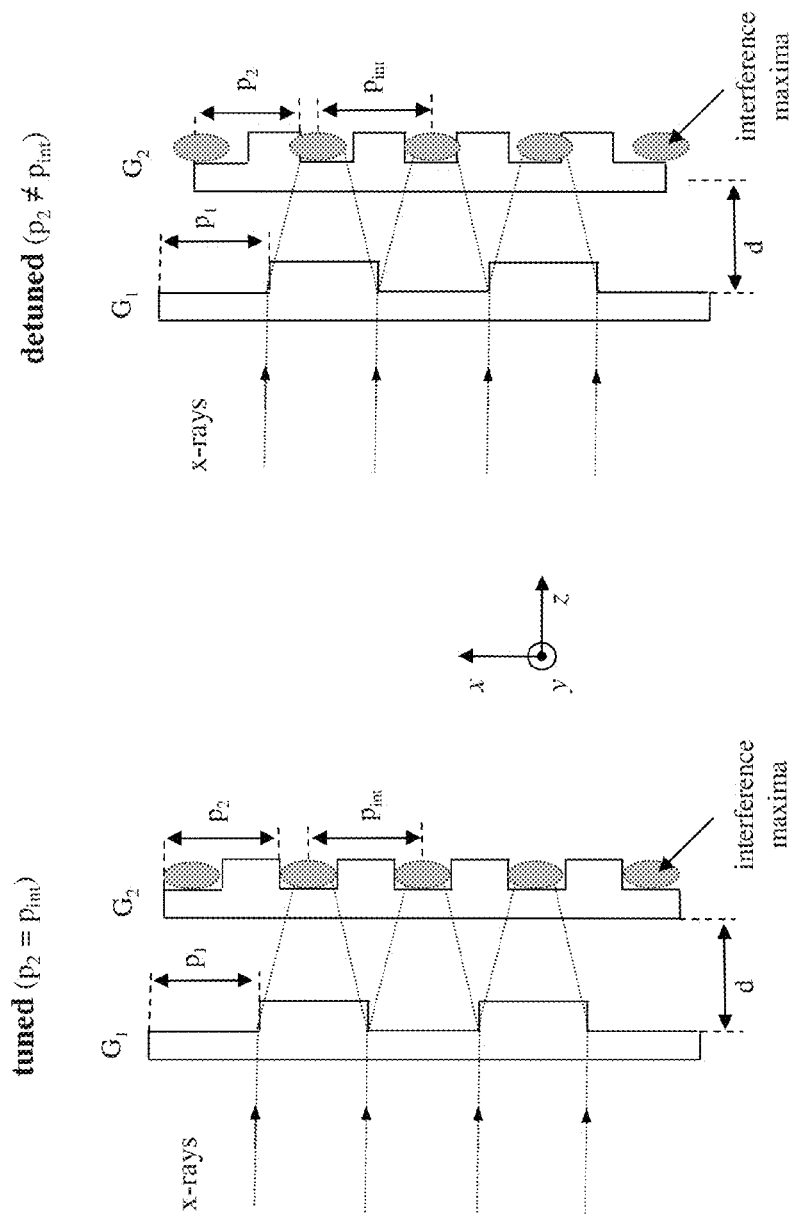
FIG. 18 is a diagram that illustrates schematics for related art tuned phase-contrast digital imaging systems and detuned phase-contrast digital imaging systems.

To implement continuous motion of the swing arm with fixed G1 and G2 gratings, exemplary embodiments of phase contrast imaging systems have to be detuned. In one exemplary embodiment, a detuned phase contrast imaging system can be understood to be an imaging system in which the pitch $p_2$ of the analyzer grating G2 is purposely controlled or fabricated to be unequal to a period of interference pattern $p_{int}$ at a Talbot distance behind the phase grating G1. In another exemplary embodiment, a detuned phase contrast imaging system can be understood to be an imaging system in which the pitch $p_2$ of the analyzer grating G2 is controlled or fabricated to be equal to a period of interference pattern $p_{int}$ at a Talbot distance behind the phase grating G1, but the analyzer grating G2 is positioned away from the corresponding Talbot distance. In certain exemplary embodiments, a detuned phase contrast imaging system can generate a periodic fringe pattern, where the fringe pattern occurs over a width or a portion of the width of the analyzer gating G2. Although a number of exposures for detuned grating based PCI system embodiments in a complete or partial scan of an object is about the same, positional errors and/or scanning time can be reduced relative to a tuned grating based PCI systems. FIG. 18 is a diagram that illustrates concepts of exemplary tuned and detuned phase contrast imaging systems. The analyzer grating G2 and the interference pattern can be approximated as a cosine waves with the frequencies $f_2=1/p_2$ and $f_{int}=1/p_{int}$, respectively. In the plane of detector, the signal can be represented by a product of G2 grating pattern and interference pattern (e.g., a product of two cosine waves: one with frequency $f_2$ and another with frequency $f_{int}$). Such a product results in a linear combination of cosines of $f_{int}+f_2$ and $f_{int}-f_2$. Due to the frequency response of the detector, the only detected signal is a signal with the frequency of $\Delta f=f_{int}-f_2$.

In the case of a tuned phase contrast imaging system ($f_{int}=f_2$), the signal is maximum. When measuring the open field in such configuration, the detector yields the uniform image. In the case of detuned phase contrast imaging system, the detected image will have a cosine pattern with a lower contrast caused by detector's MTF. The loss of the contrast depends on how strongly the system is detuned, i.e. $\Delta f=f_{int}-f_2$. FIG. 19 is a diagram that illustrates examples of the open field images measured in the detector plane for tuned and detuned configurations of a phase contrast imaging system embodiment. As shown in FIG. 19, an open field image for a tuned phase contrast imaging system embodiment can produce an unchanging or flat open field image across the analyzer grating G2. As shown in FIG. 19, the lateral size of an image is chosen to be equal to one period of fringe pattern as an example.

In certain exemplary methods and/or apparatus embodiments, material identification or decomposition can be obtained using tomosynthesis imaging systems. Although reconstructions using tomosynthesis imaging systems may have less granularity or inconsistent z-directional data relative to x-directional and y-directional data, material identification or decomposition can be obtained for a prescribed or selected slice as described herein.

Exemplary embodiments herein can be applied to digital radiographic imaging panels that use an array of pixels comprising an X-ray absorbing photoconductor and a readout circuit (e.g., direct detectors). Since the X-rays are absorbed in the photoconductor, no separate scintillating screen is required.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of radiographic imaging systems and/methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method for digital radiographic image reconstruction of an object, executed at least in part on a computer, comprising:
   obtaining a first plurality of 2D projection images over a range of scan angles;
   obtaining a second plurality of 2D projection images over a range of scan angles;

generating at least two statistically independent reconstructed images of a portion of an object from the first plurality of 2D projection images and the second plurality of 2D projection images;

determining a material property for each of at least two materials represented in the projection images;

using a conditional likelihood determination comprising the material property for said each of at least two materials and the at least two statistically independent reconstructed images to differentiate the at least two materials as a function of volume in a reconstructed image of the portion of the object; and storing the reconstructed image of the portion of the object having the at least two materials differentiated in a computer-accessible memory.

2. The method of claim 1, where the material property for said each of at least two materials is individually determined by numeric modeling using composition by weight or empirically modeled.

3. The method of claim 1, where the reconstructed image of the object that has been differentiated among the at least two materials is a visible 2D reconstructed image or a visible 3D reconstructed volume of the object.

4. The method of claim 1, where the conditional likelihood determination for material differentiation is performed in a single scan PCI CT.

5. The method of claim 1, where the conditional likelihood determination for material differentiation is performed in spectral PCI CT, where a plurality of x-ray exposures at different energies is used with an integrating detector or a single x-ray exposure is used with an energy-resolving detector.

6. The method of claim 1, where the conditional likelihood determination for material differentiation is performed in absorption-based spectral CT, where plurality of x-ray exposures at different energies is used or the energy-resolving detector is used.

7. The method of claim 1, where the conditional likelihood determination for material differentiation is determined on a pixel-by-pixel basis.

8. The method of claim 1, where the conditional likelihood determination for material differentiation is determined at more than one pixel at a time.

9. The method of claim 1, where at least two differentiated materials comprise adipose tissue, glandular tissue, skin tissue, calcification material and tumor tissue.

10. The method of claim 1, where the at least two statistically independent reconstructed images comprise phase image data and attenuation image data or the at least two statistically independent reconstructed images comprise attenuation image data at different mean energies.

11. The method of claim 1, where an energy resolving detector is used and the number of statistically independent reconstructed images at least doubles.

12. The method of claim 1, further comprising:
storing a 3D volume image reconstruction in the computer-accessible memory, wherein the 3D volume image reconstruction is a mammography image, an orthopedic medical image, a dental medical image, a pediatric medical image or generated by image data from a flat panel detector.

13. The method of claim 1, where the subject is a breast, a limb, an extremity, a weight bearing extremity or a portion of a dental arch.

14. The method of claim 1 wherein an image reconstruction is based on an examination type or x-ray radiation source exposure setting.

15. The method of claim 1, comprising processing the plurality of projection images by:
performing one or more of geometric correction, scatter correction, beam-hardening correction, and gain and offset correction on the plurality of 2D projection images;
performing a logarithmic operation on the scatter corrected plurality of 2D projection images to obtain line integral data; and
performing a row-wise ramp linear filtering to the line integral data.

16. A method for digital radiographic image reconstruction of an object, executed at least in part on a computer, comprising:
obtaining a first plurality of 2D projection images over a range of scan angles;
obtaining a second plurality of 2D projection images over a range of scan angles, where the second plurality of 2D projection images is statistically independent of the first plurality of 2D projection images;
obtaining at least two reconstructed images of a portion of an object based on the first plurality of 2D projection images and the second plurality of 2D projection images;
obtaining a material property as a function of radiation energy for each of at least two materials represented in the projection images;
using a conditional likelihood determination comprising applying the material property to the at least two statistically independent reconstructed images to differentiate the at least two materials as a function of position in a reconstructed image of the portion of the object; and
storing the reconstructed image of the portion of the object having the at least two materials differentiated in a computer-accessible memory.

17. The method of claim 16, where the material property comprises attenuation as a function of energy per unit length and phase shift as a function of energy per unit length or the attenuation and phase shift in standard units, where the attenuation or the phase shift is determined through a calibration procedure.

18. The method of claim 16, where the conditional likelihood determination comprises combining a first conditional determination in a first reconstructed image of the portion of the object for said each of the at least two materials with a second conditional determination in a second reconstructed image of the portion of the object for said each of the at least two materials to differentiate the at least two materials as a function of position in a reconstructed image of the portion of the object, further comprising weighting the first conditional determination relative to the second conditional determination.

* * * * *